United States Patent [19]

Manara et al.

[11] 4,254,296

[45] Mar. 3, 1981

[54] PROCESS FOR THE PREPARATION OF TERTIARY OLEFINS

[75] Inventors: Giovanni Manara; Vittorio Fattore; Marco Taramasso; Bruno Notari, all of San Donato Milanese, Italy

[73] Assignee: Snamprogetti S.p.A., Milan, Italy

[21] Appl. No.: 46,253

[22] Filed: Jun. 7, 1979

[30] Foreign Application Priority Data

Jun. 22, 1978 [IT] Italy .............................. 24845 A/78

[51] Int. Cl.$^3$ .............................................. C07C 1/00
[52] U.S. Cl. .................................... 585/640; 585/733
[58] Field of Search ......................................... 585/640

[56] References Cited

U.S. PATENT DOCUMENTS

| | | | |
|---|---|---|---|
| 3,170,000 | 2/1965 | Verdol | 585/640 |
| 4,006,198 | 2/1977 | Tesei et al. | 585/640 |
| 4,072,732 | 2/1978 | Hargis et al. | 585/640 |
| 4,072,733 | 2/1978 | Hargis et al. | 585/640 |

*Primary Examiner*—Curtis R. Davis
*Attorney, Agent, or Firm*—Morgan, Finnegan, Pine, Foley & Lee

[57] ABSTRACT

A process is disclosed for preparing tertiary olefins having a high degree of purity and in good yields starting from tertiary ethers such as methyltert.butyl ether and in which the improvement comprises using an extremely efficient catalyst system which consists of a crystalline silica having a high specific surface area and which has been modified by an oxide of a metallic cation having an at least partially amphoteric character. Such catalyst may be, if appropriate, accompanied by an alumina-modified silica as an adjuvant co-catalyst.

10 Claims, 3 Drawing Figures

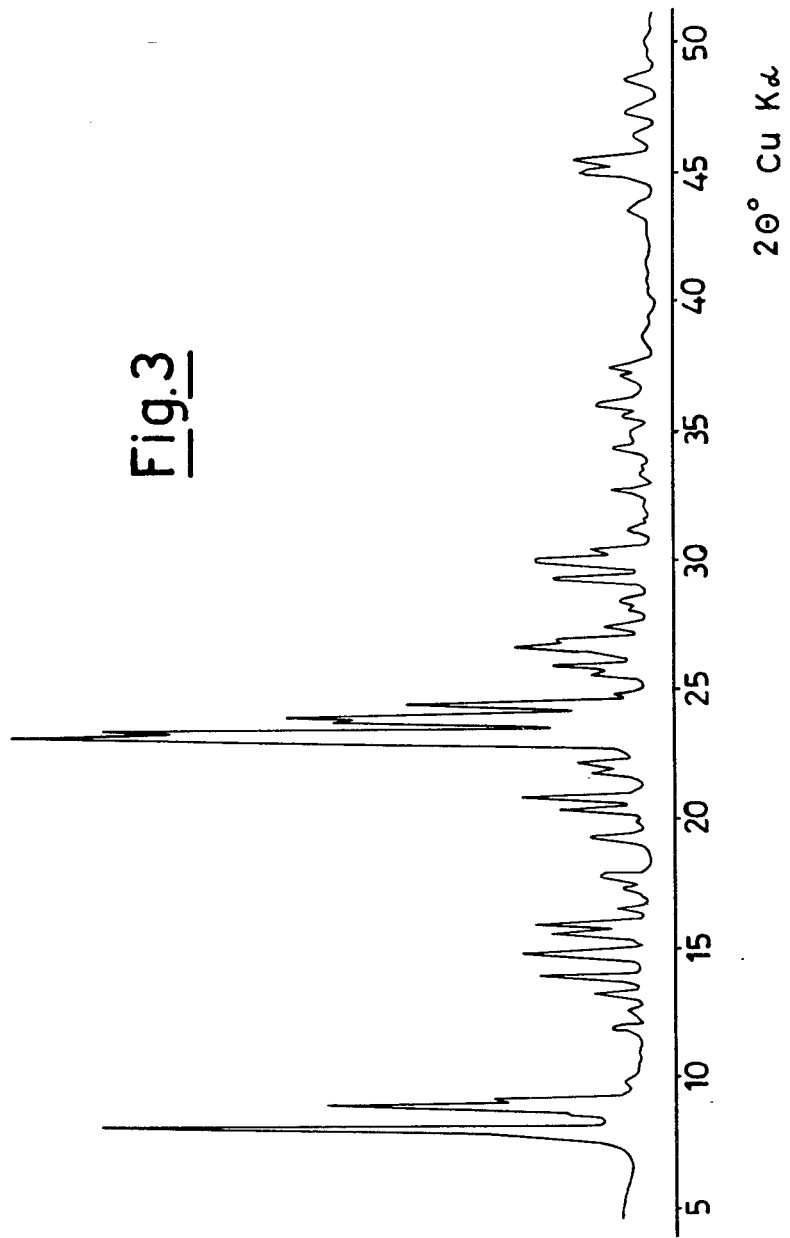

PROCESS FOR THE PREPARATION OF TERTIARY OLEFINS

BACKGROUND OF THE INVENTION

This invention relates to a process for the preparation of pure tertiary olefins starting from their corresponding tertiary ethers.

It is known that by reacting a low-molecular weight alcohol with a mixture of olefins the tertiary olefins only enter reaction to form alkyl-tert.alkyl-ethers, inasmuch as the other olefins either react very slowly or remain completely unaffected.

Tertiary olefins are very important starting materials for the preparation of polymers and chemicals, so that it is of the utmost importance to succeed in isolating them in the purest possible form.

Methods for the obtention of tertiary olefins are known. For example, a few methods are based on the use of $H_2SO_4$; but, in addition to the corrosion and pollution problems, in methods where the acid is used there are a number of other shortcomings, among which the requirement of concentrating the acid prior to recycling is one of the most important. Other methods are based on the decomposition of the corresponding methyl ethers in the presences of suitable catalytic systems.

However, the use of the catalysts suggested heretofore for carrying out such a reaction is conducive, in the majority of the cases, to the formation of dialkyl ethers as a consequence of the dehydration of the corresponding primary alcohols.

While such a reaction is faster, the higher the working temperature a few if the conventional catalysts require the use of comparatively high temperatures, a fact which leads to the loss of alcohol and the attendant necessity of feeding fresh alcohol to the initial etherification reaction.

Moreover, the formation of dialkyl ethers necessitates more intricate installations since a separation of the dialkyl ethers from the tertiary olefin is imperative. Furthermore, the formation of a considerable amount of dialkyl ether necessitates also the dehydration of the primary alcohol prior to recycling the same, otherwise the admixture of phases is experienced in the etherification reaction and the formation of tertiary alcohols might take place.

Another drawback which is experienced when the reaction is carried out beyond certain temperature levels is the occurrence of dimerization and trimerization of the tertiary olefin which is recovered from the decomposition of the ethers.

A few of the mentioned defects can be offset when the modification reaction of the tert.alkyl ethers is carried out in the presence of a catalytic system composed of an active alumina which has been modified by partially substituting silanol groups for the superficial —OH groups, according to the teaching of our Italian Pat. No. 1,001,614 of Apr. 4, 1976. Nevertheless, the modified active alumina made according to the teaching of the aforementioned patent gives rise, when a strong temperature increases in the reaction temperature is experienced, to the formation of dialkyl ether, the result being a poorer recovery of the primary alcohol to be recycled.

It has been found that the shortcomings of the conventional art can be overcome and, most important, that a recovery of methanol of over 90% can be achieved irrespective of the working temperatures which can even exceed 400° C., and which also occurs in a complete absence of any secondary reactions.

It has also been found that it is possible to prepare the tertiary olefins in a state of purity and in a high yield, starting from the tert. Alkyl ethers mentioned above, by contacting the ether concerned with a particular catalyst system. The ether is thus decomposed into the olefin and the corresponding low molecular weight alcohol and the latter in recycled and again reacted with a mixture of olefins.

In accordance with the present invention there is provided a process for the preparation of tertiary olefins starting from the corresponding tert.alkyl ethers, more particularly isobutene from methyl tert.butyl ether, said process being characterized in that a catalyst is used, which is selected from among a crystalline silica which has been modified or unmodified with oxides of metal cations and which corresponds a high specific surface area and corresponding to the following general formula: $0–1M_nO_m \cdot 1SiO_2$, more particularly $0.0001–1M_nO_m \cdot 1SiO_2$, wherein $M_nO_m$ is the oxide of a metallic cation capable of entering the silica lattice as a substituent for silicon or as a salt of polysilicic acids, and/or a silica which has been modified with alumina and corresponds to the following general formula:

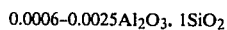

$$0.0006–0.0025 Al_2O_3 \cdot 1SiO_2$$

wherein the quantity of alumina which has been introduced enables the catalytic activity to be monitored.

DESCRIPTION OF THE PREFERRED EMBODIMENT

Small amounts of water may be present in the compound, in a proportion which is a function of the firing temperature. These silicas can further be modified with respect to their dehydrating power by the addition of sodium or potassium.

Silicas which contain higher amounts of aluminum have too pronounced a dehydrating power and convert the alcohol into an ether, so that the recovery of alcohol is lowered to economically unacceptable ranges.

Among the metallic cations suitable for replacing silicon preference should be given to those elements which have, or partially amphoteric, an amphoteric nature, such as chromium, beryllium, titanium, vanadium, manganese, iron, cobalt, zinc, zirconium, rhodium, silver, tin, antimony and boron.

The crystalline silicas employed in the practice of this invention have a specific surface area over 150 m²/g (square meters per gram), and preferably a specific surface area in the range 200 to 500 m²/g.

Figure 1:
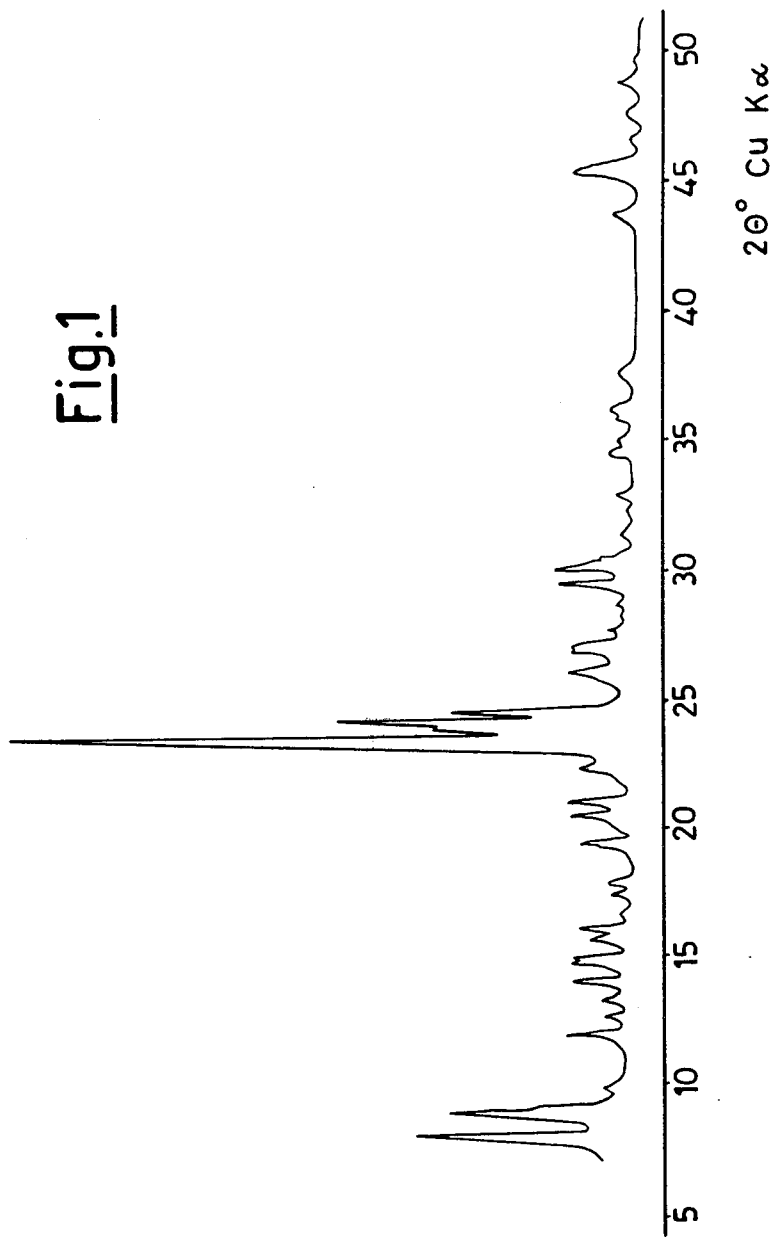
Figure 2:
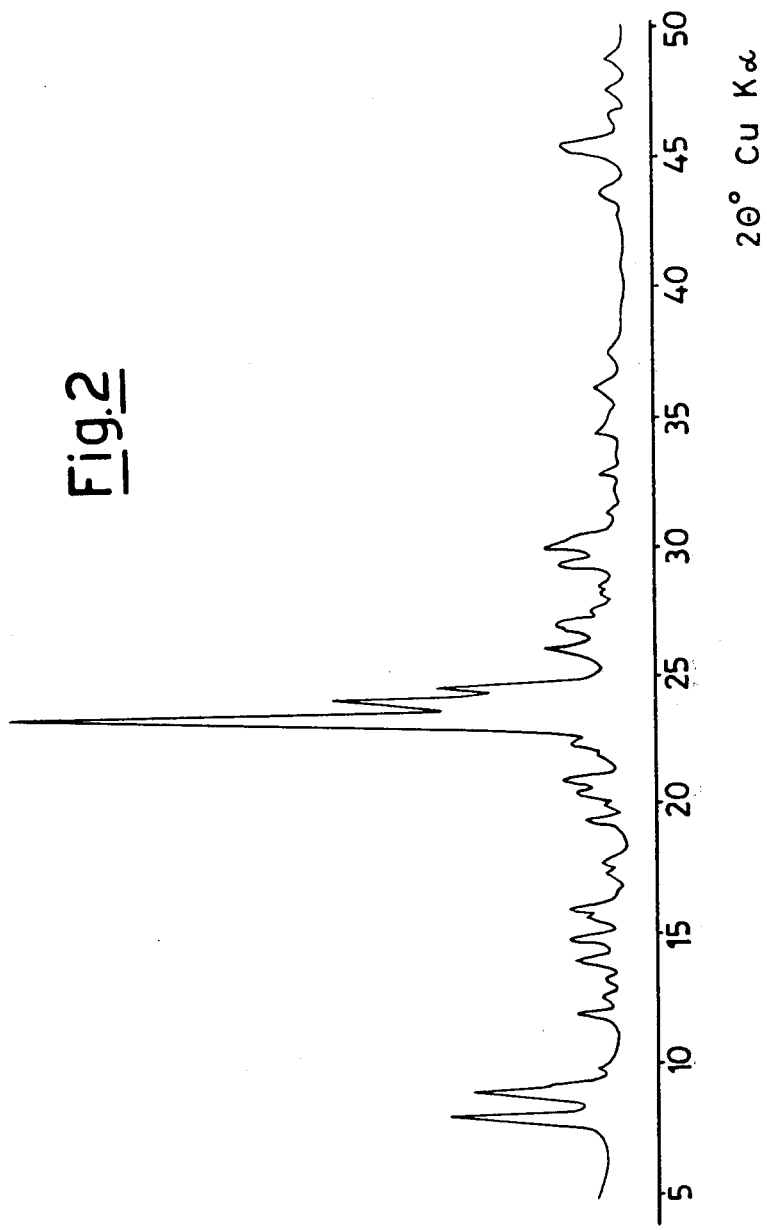

FIGS. 1 and 2 of the accompanying drawings show two typical X-ray diffraction spectra of modified silicas employed in the practice of the present invention.

The aluminum-modified silicas employed in the practice of the present invention also have a specific surface area over 150 m²/g, in general between 200 and 500 m²/g.

FIG. 3 of the accompanying drawings show a typical X-ray diffraction spectrum of aluminum-modified silicas employed in the practice of the present invention.

Although the decomposition reaction of the tert.alkyl ethers takes place with satisfactory yields under atmospheric pressures, it is preferred, however, to work under slightly superatmospheric pressures in order to be able to use cooling water without any other expedient so that condensation of the products obtained may be carried out directly.

As a rule, pressures varying from 1 to 10 kg/cm² (kilograms per square centimeter) are employed, the preference being for a pressure which equals, at least, the vapor pressure of the olefin to be recovered, at the predetermined condensation temperature. The reaction is carried out at temperatures below, or equal, to 500° C., and preferably in the range of from 130° C. to 350° C.

The reaction is carried out at a space velocity, expressed in terms of volume of liquid per volume of catalyst per hour, or LHSV (Liquid Hourly Space Velocity) between 0.5 and 200, and preferably in the range of from 1 to 50.

The primary alcohols which can be recovered upon completion of the decomposition run according to this invention contain, preferably from 1 to 6 carbon atoms.

The process of the present invention can be adapted to the recovery of tertiary olefins from olefin mixtures of from $C_4$ to $C_7$, such as, for example, those which come from thermal cracking, steam cracking or catalytic cracking.

Among the several tertiary olefins which can be obtained in a pure state, there one isobutylene, isoamylenes, such as 2-methyl-2-butene and 2-methyl-1-butene, isohexenes such as 2,3-dimethyl-1-butene, 2,3-dimethyl-2-butene, 2-methyl-1-pentene, 2-methyl-2-penetene, 3-methyl-2-penetene (both cis- and trans- ), 2-ethyl-1-butene and 1-methyl-cyclopentene, and, also, the tertiary isoheptenes.

The conversion of the tert. alkyl ether into primary alcohol and olefin is virtually a quantitative one.

No formation of dimers and trimers of the recovered tertiary olefin is experienced, or formation of tertiary alcohol.

THE EXAMPLES

The mode of operation and the advantages of the process of the present invention will become more clearly apparent from the following illustrative examples, which are non-limitive of for the invention.

EXAMPLE 1

This example is for the purpose of illustrating the activity, in the decomposition of the methyl-tert.butyl ether, of the crystalline silica as modified by TRS-23 aluminum, thoroughly washed so that the proton concentration, per gram of catalyst, is $4.3 \times 10^{-3}$ meq (i.e. milliequivalents), and so that the protonic concentration of the sodium-containing catalyst is $1.1 \times 10^{-5}$ meq.

The TRS-23 catalyst is prepared as follows:

A Pyrex-glass vessel which is kept continuously in a nitrogen atmosphere is charged with 80 g of tetraethyl orthosilicate (TEOS) which are heated with stirring to a temperature of 80° C. There are then added, 68 mls of a 25% (by wt) aqueous solution of tetraethylammonium hydroxide, stirring being maintained, at 80° C. until such time as the mixture becomes homogeneous and clear. Subsequently, 80 mg (milligrams) of $Al(NO_3)_3 \cdot 9H_2O$, dissolved in 50 mls of abs. ethanol, and 2 g of NaOH (granular) dissolved in 10 mls of distilled water, are added. A compact gel is formed, to which distilled water is added to make up a total volume of 200 mls. Stirring is accelerated and the mixture is brought to a boil in order to complete hydrolysis and to drive off all of the ethanol, that is both the added ethanol and the ethanol set free by the hydrolysis.

The gel is slowly and gently converted into a white power which is the precursor of the crystalline silica.

The volume is made up to 150 mls with distilled water, after which the Pyrex-glass vessel is introduced into an autoclave and is allowed to stand at a temperature of 155° C. for 18 days.

Upon cooling, the solid which is formed is centrifuged at 10,000 rpm for 15 minutes, the cake is reslurried in distilled water and centrifuged again: This washing operation is repeated four times. The product is oven-dried at 120° C. and subjected to X-rays which indicate that it is crystalline.

The solid is then fired for 16 hours at 550° C. in an airstream and the concentration or protonic milliequivalents per gram of the sample is determined as $1.1 \times 10^{-5}$.

To remove the alkalies which are still present therein, the sample is washed repeatedly by slurrying in boiling distilled water which contains ammonium acetate dissolved therein. The sample is then again fired at 550° C., for 6 hours. Chemical analysis on the thusly obtained sample indicates the following composition:

| | |
|---|---|
| % by wt of $SiO_2$ | 96.3 |
| % by wt of $Al_2O_3$ | 0.2 |
| % by wt of $Na_2O$ | 0.03 |
| Loss on firing at 1100° C. | 3.47% |
| $SiO_2/Al_2O_3$ molar ratio is | 817 |

The specific surface area, as determined by the BET Method is 470 m²/g (BET stands for Brunauer Emmett Teller).

In an electrically heated tubular reactor having a diameter of 8 mm (millimeters), there are introduced 4 mls, i.e. 2.8 g of the catalyst prepared as set forth above and having a particle size of from 30 to 80 mesh (ASTM, USA series).

A charge of methyl-tert.butyl ether is introduced into the reactor through a metering pump after being heated by flowing it through a preheating tube.

Downstream of the reactor, there are arranged a check valve calibrated to 6 bars and a sampling system which is properly heated and which permits, upon reduction of the pressure, that the introduction of reaction effluent into a gas chromatograph.

The catalyst is heated to 550° C. for 2 hours, on the presence of a stream of anhydrous nitrogen to remove the adsorbed water prior to feeding in the methyl-tert.butyl ether into the reactor.

There are charged, at the outset, 2.5 mls of TRS-23 catalyst having a protonic concentration of $4.3 \times 10^{-3}$ meq/g, having a particle size of from 30 to 80 mesh (ASTM, USA series). Methyl-tert.butyl ether is fed into the reactor at a rate of flow of 6.66 ml/h, 10 ml/h and 20 ml/h (milliliters an hour), which correspond to LHSVS of 2.66, 4, and 8, respectively. The results which were obtained are set forth in TABLE 1 along with the test conditions.

TABLE 1

| | TRS-23 CATALYST | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2.65 | 6 | 180 | 99.0 | 99.7 | 99.6 |

TABLE 1-continued

| | TRS-23 CATALYST | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 2 | 4 | 6 | 185 | 98.7 | 99.7 | 99.6 |
| 3 | 8 | 6 | 180 | 78.2 | 100 | 99.8 |
| 4 | 8 | 6 | 192 | 91.7 | 99.9 | 99.8 |
| 5 | 8 | 6 | 200 | 92.6 | 99.9 | 99.3 |
| 6 | 8 | 6 | 215 | 98.4 | 99.9 | 99.3 |

Subsequently, 4 mls of the same TRS-23 catalyst (but containing sodium) are used, the protonic concentration per g of the catalyst being $1.1 \times 10^{-5}$.

There are introduced 8 ml/h of methyl-tert.butyl ether, so as to have a space velocity (LHSV) of 2.

The results, as obtained with oven temperatures of 380° C., are tabulated in TABLE 2 below.

TABLE 2

| | TRS-23 CATALYST | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2 | 6 | 380 | 80.5 | 99.9 | 99.8 |
| 2 | 2 | 6 | 420 | 98.5 | 99.1 | 99.2 |

EXAMPLE 2

This Example is for the purpose of illustrating the activity, in the decomposition reaction of methyl-tert-.butyl ether, of TRS-28 crystalline silica which has been modified with chromium and which contains sodium so that the protonic concentration per g of catalyst is $1.2 \times 10^{-5}$ meq. The TRS-28 catalyst was prepared as follows:

A Pyrex-glass vessel kept in a nitrogen atmosphere is charged with 40 g of tetraethyl orthosilicate (TEOS) and brought to a temperature of 80° C. with stirring. There are added 20 g of a 20% aqueous solution of tetrapropylammonium hydroxide and stirring at 80° C. is continued until the mixture becomes clear, which takes about one hour.

At this stage, there are added 4 g of $Cr(NO_3)_3 \cdot 9H_2O$, dissolved in 50 mls of anhydrous ethanol. A compact, pale-green gel is formed nearly instantaneously. These are added to the gel with stirring 0.25 g of KOH dissolved in 20 mls of water. The mixture is brought to a boil while stirring in order to complete the hydrolysis and to dispel by evaporation both the added methanol and the ethanol formed during hydrolysis. These operations take 2 or 3 hours and the gel is smoothly and slowly converted into a pale-green powder which is the precursor of the chromium crystalline silica.

The manipulations are those of Example 1 hereof, the only difference being that a temperature of 155° C. and a time of 13 days are employed. The product, dried at 120° C., is subjected to X-ray crystalline. Its X-ray diffraction spectrum is shown in FIG. 1.

Chemical analysis of the sample, fired at 550° C., indicates the following composition:

| | |
|---|---|
| % by wt of $SiO_2$ | 90.5 |
| % by wt of $Cr_2O_3$ | 6.0 |
| Loss on firing at 1100° C. | 3.5% |

The molar ratio $SiO_2/Cr_2O_3$ of the sample is 38. The specific surface area is 380 m²/g.

The same reactor as used in Example 1 is charged with 3 mls of the catalyst, prepared as set forth above, having a particle size between 30 and 80 mesh (ASTM, USA series).

Operating as in Example 1 and, after heating for 2 hours to 550° C. in an anhydrous nitrogen stream to remove water, methyl-tert.butyl ether is fed thereto at a rate of flow of 6.6 mls/h, that is at a space velocity, LHSV, of 2.2 at different temperatures. The results are set forth in TABLE 3 below.

TABLE 3

| | TRS-28 CATALYST | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2.2 | 6 | 300 | 43.6 | 99.9 | 99.4 |
| 2 | 2.2 | 6 | 350 | 80.1 | 99.9 | 99.4 |
| 3 | 2.2 | 6 | 400 | 93.6 | 99.9 | 99.3 |

EXAMPLE 3

This Example is for the purpose of illustrating the activity, in the decomposition reaction of methyl tert-.butyl ether, of TRS-28 catalyst which has been thoroughly washed so that the protonic concentration per g of catalyst is $5.8 \times 10^{-3}$ milliequivalents. The reactor of Example 1 hereof is charged with 1.5 ml (i.e. 0.51 g) of catalyst having a particle size between 30 and 80 mesh (ASTM, USA series).

Operating as in Example 1, after heating for 2 hours to 550° C. in a stream of anhydrous nitrogen to remove water, methyl-tert.butyl ether is fed into the reactor at rates of flow of 3.3, 6.6, 10, 20, 30, 60 and 120 ml/h, the respective space velocities (LHSV) being 2.2, 4.4, 6.7, 13.3, 20, 40 and 80, at different oven temperatures. The results obtained are set forth in TABLE 4 below.

TABLE 4

| | TRS-28 CATALYST | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2.2 | 6 | 200 | 99.4 | 99.8 | 99.3 |
| 2 | 4.4 | 6 | 215 | 98.1 | 99.9 | 99.3 |
| 3 | 6.7 | 6 | 215 | 67.8 | 99.9 | 99.4 |
| 4 | 6.7 | 6 | 230 | 96.3 | 99.9 | 99.3 |
| 5 | 13.3 | 6 | 250 | 93.4 | 99.9 | 99.3 |
| 6 | 13.3 | 6 | 260 | 96.2 | 99.9 | 99.4 |
| 7 | 13.3 | 6 | 270 | 97.8 | 99.9 | 99.5 |
| 8 | 20.0 | 6 | 270 | 75.8 | 99.9 | 99.6 |
| 9 | 20.0 | 6 | 315 | 95.3 | 99.9 | 99.5 |
| 10 | 40.0 | 6 | 360 | 91.9 | 99.9 | 99.5 |

EXAMPLE 4

This Example is for the purpose of illustrating a activity of the beryllium-modified crystalline silica, TRS-27, having a protonic concentration of $1.5 \times 10^{-3}$ milliequivalents per g of catalyst.

The reactor of Example 1 is charged with 2 mls of TRS-27 catalyst having a particle size between 30 and 80 mesh (ASTM, USA series).

The TRS-27 catalyst was prepared as set forth in Example 1 by reacting 40 g of tetraethyl orthosilicate with 100 mls of a 20% (by wt) aqueous solution of tetrapropylammonium hydroxide and 4 g of Be(NO$_3$)$_2$.4H$_2$O, dissolved in 80 mls of ethanol.

The mixture is maintained at a temperature of 155° C. for 17 days.

The product, dried at 120° C. is subjected to X-rays which indicates that it is crystalline. Its X-rays which indicates that it is diffraction spectrum is shown in FIG. 2.

Chemical analysis of the sample, fired at 550° C. indicates the following composition:

| | |
|---|---|
| SiO$_2$ | 92.68%, on a weight basis |
| BeO | 3.2% |
| Na$_2$O | 0.02% |

Loss on firing at 1100° C.: 4.1%, by wt. The molar ratio SiO$_2$/BeO of the sample is 12.

Operating as in Example 1, upon heating for 2 hours to 550° C. in a stream of dry nitrogen to remove water from the catalyst, the methyl-tert.butyl ether is introduced into the reactor under the conditions set forth in TABLE 5 below, which also sets forth the results obtained.

TABLE 5

TRS-27 CATALYST

| Test run No. | Space velocity LHSV | Pressure bar | Oven temp. °C. | Conversion methyl-tert. butylether % | Methanol recovery % | Isobutene recovery % |
|---|---|---|---|---|---|---|
| 1 | 2 | 6 | 180 | 73.8 | 99.9 | 100 |
| 2 | 2 | 6 | 195 | 94.2 | 99.9 | 99.5 |
| 3 | 2 | 6 | 205 | 98.7 | 99.9 | 99.5 |
| 4 | 2 | 6 | 220 | 99.7 | 99.8 | 99.5 |
| 5 | 2 | 6 | 240 | 100 | 99.6 | 99.2 |
| 6 | 5 | 6 | 230 | 84.0 | 99.9 | 99.6 |
| 7 | 5 | 6 | 255 | 99.8 | 99.9 | 99.5 |
| 8 | 5 | 6 | 270 | 99.8 | 99.9 | 99.5 |
| 9 | 5 | 6 | 300 | 99.9 | 99.5 | 99.2 |
| 10 | 7.5 | 6 | 300 | 99.9 | 99.4 | 99.2 |
| 11 | 15 | 6 | 300 | 95.6 | 99.7 | 99.1 |
| 12 | 30 | 6 | 300 | 77.3 | 99.9 | 99.1 |
| 13 | 30 | 6 | 355 | 98.4 | 99.8 | 99.1 |
| 14 | 75 | 6 | 380 | 93.4 | 99.8 | 99.1 |
| 15 | 75 | 6 | 395 | 96.4 | 99.8 | 99.1 |

EXAMPLE 5

This Example is for the purpose of illustrating the activity of aluminum-modified TRS-57 crystalline silica with a concentration of $1.5 \times 10^{-1}$ meq of H$^+$ per gram of catalyst.

The TRS-57 catalyst was prepared in accordance with the procedure of Example 1 by reacting 240 g of tetraethyl orthosilicate, 240 mg of Al(NO$_3$)$_3$.9H$_2$O dissolved in 150 mls. of abs. ethanol, a solution of 81 g of triethanolamine in 150 mls of distilled water and 21 g of sodium hydroxide at a temperature of 194° C. for 7 days.

The product dried at 120° C. is X-ray crystalline. Its X-ray diffraction spectrum is shown in FIG. 3.

Chemical analysis of the thusly obtained sample indicates the following composition:

| | |
|---|---|
| % by wt of SiO$_2$ | 96.2 |
| do Al$_2$O$_3$ | 0.2 |
| do Na$_2$O | 0.05 |
| Loss on firing at 1100° C. | 3.55% |
| The molar ratio SiO$_2$/Al$_2$O$_3$ is | 816 |

The specific surface area, as determined by the BET method is 344 m$^2$/g and the concentration of milliequivalents H$^+$ per g of sample is $1.5 \times 10^{-1}$.

The thusly obtained crystalline powder is extruded, upon addition thereto of 10% of colloidal silica as a binder, and slugs are obtained having a diameter of 3 mm and a height of 4 mm. The slugs after having been fired again at 500° C. for 4 hours, are introduced into a tubular reactor having an inside diameter of 20 mm which is also charged with 40 mls of the catalyst obtained as disclosed hereinabove. Methyl-tert. butyl ether introduced into the reactor with the aid of a metering pump is preheated by flowing it through a preheating tube having an inside diameter of 4 mm and a length of 1 meter. The temperature of the preheater and that of the reactor are controlled by a thermostatic bath containing a silicone oil. Down-stream of the reactor, there is disposed a check-valve calibrated at 6 bar and a system for collecting the product, which is cooled with dry ice.

The charge is fed into the reactor at the space velocities (LHSV) and at the bath temperatures set forth in TABLE 6 below.

TABLE 6

| Test rum No. | Space velocity LSHV | Pressure bar | Bath temp. °C. | Conversion methyl-tert. butylether % | Methanol recovery % | Isobutene recovery % |
|---|---|---|---|---|---|---|
| 1 | 5 | 6 | 150 | 90.9 | 99.9 | 99.8 |
| 2 | 10 | 6 | 160 | 90.6 | 99.9 | 99.8 |
| 3 | 30 | 6 | 290 | 97.9 | 99.9 | 99.8 |
| 4 | 60 | 6 | 340 | 94.7 | 99.9 | 99.8 |
| 5 | 150 | 6 | 390 | 94.6 | 99.9 | 99.8 |

EXAMPLE 6

(A comparison example)

This Example is for the purpose of illustrating the activity, in the decomposition of methyl-tert.butyl ether, of a commercial silica for fluid beds, having a specific surface area of 419 m$^2$/g and a sodium oxide content of 0.08%, alumina content of 0.03% and sulphates content of 0.14% by wt., with a protonic concentration, per gram of catalyst, of $4.8 \times 10^{-3}$ meq. The reactor of Example 1 is charged with 4 mls of a catalyst having a particle size of between 30 and 100 mesh (ASTM, USA series).

Operating as in Example 1 and, upon heating for 2 hours at 500° C. in a stream of dry nitrogen to remove the water retained in the catalyst, methyl-tert.butyl ether is fed into the reactor at a rate of flow of 8 ml/h, that is, at a space velocity, LHSV, of 2, at the temperatures set forth in TABLE 7. This Table also set forth the test results.

TABLE 7

Catalyst : A commercial silica for fluid beds.

| Test run No. | Space velocity LHSV | Pressure bar | Oven temp. °C. | Conversion methyl-tert. butylether % | methanol recovery % | Isobutene recovery % |
|---|---|---|---|---|---|---|
| 1 | 2 | 6 | 195 | 47.8 | 99.7 | 98.2 |
| 2 | 2 | 6 | 215 | 71.6 | 99.3 | 98.4 |
| 3 | 2 | 6 | 225 | 78.5 | 99.0 | 98.9 |
| 4 | 2 | 6 | 240 | 83.6 | 98.5 | 99.0 |
| 5 | 2 | 6 | 255 | 89.8 | 98.0 | 99.0 |

EXAMPLE 7

(A comparison example)

This Example is for the purpose of illustrating the activity in the decomposition reaction of methyl-tert-.butyl ether of a pelletized commercial silica having a specific surface area of 147 m$^2$/g and a sodium oxide content of 0.36%, alumina content of 0.48% and sulphates content of 0.4% by wt, with a protonic concentration of $1\times10^{-4}$ milliequivalents (meq) per g of catalyst. The reactor of Example 1 is charged with 4 mls of properly ground catalyst having a particle fraction between 30 and 80 mesh size (ASTM, USA series).

Operating as in Example 1 and upon heating for 2 hours at 500° C. in a stream of dry nitrogen to remove the water held in the catalyst, methyl-tert.butyl ether is fed into the reactor at a rate of flow of 8 ml/h, which corresponds to a space velocity, LHSV, of 2, the oven temperatures being 210° C. and 300° C. as set forth in TABLE 8. The Table also set forth the test results.

TABLE 8

| | Catalyst : A pelletized commercial silica. | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2 | 6 | 210 | 2.6 | 99.9 | 90.6 |
| 2 | 2 | 6 | 300 | 43.1 | 99.9 | 96.4 |

EXAMPLE 8

(A comparison example)

This Example is for the purpose of illustrating the activity in the decomposition reaction of methyl-tert-.butyl ether of an extruded commercial silica having a specific surface area of 111 m$^2$/g and a sodium oxide content of 0.45%, alumina content 0.52% and sulphates content of 0.4%, by wt. with a protonic concentration, per g of catalyst, of $1.1\times10^{-5}$ milliequivalents (meq).

The reactor of Example 1 is charged with 4 mls of catalyst, which have properly been milled to provide a particle fraction of between 30 and 80 mesh (ASTM, USA series).

Operating as in Example 1 and, upon heating for 2 hours at 500° C. in a dry nitrogen stream to remove the water retained in the catalyst, methyl-tert.butyl ether is fed into the reactor at a rate of flow of 8 ml/h, which corresponds to a space velocity, LHSV, of 2, the oven temperatures being 210° C. and 315° C., as set forth in Table 9 below.

TABLE 9

| | Catalyst : extruded commercial silica. | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2 | 6 | 210 | 1.5 | 99.9 | 97.0 |
| 2 | 2 | 6 | 315 | 18.5 | 99.9 | 98.2 |

EXAMPLE 9

(A comparison example)

This example is for the purpose of illustrating the activity, in the decomposition reaction of methyl-tert-.butyl ether, of a silica-gel of a commercial type, granulated and having a specific surface area of 400 m$^2$/g and a sodium oxide content of 0.06%, alumina content of 0.10% and calcium oxide content of 0.03%, with a protonic concentration, per g of catalyst, of $1\times10^{-3}$ meq.

The reactor of Example 1 is charged with 4 mls of catalyst which were previously dehydrated overnight at 500° C. and were milled to provide a particle fraction of between 30 and 80 mesh (ASTM, USA series), Operating as in Example 1 and after an additional heating stage for 2 hours at 500° C. under a nitrogen stream to drive off the residual water from the catalyst, methyl-tert.butyl ether is fed into the reactor at a rate of flow of 8 ml/h (milliliters an hour), which corresponds to a space velocity, LHSV, of 2, the oven temperatures being those set forth in TABLE 10 together with the test results data.

TABLE 10

| | Catalyst : A granular commercial silica. | | | | | |
|---|---|---|---|---|---|---|
| Test run No. | Space velocity LHSV | Pressure bar | Oven temp. °C. | Conversion methyl-tert. butylether % | Methanol recovery % | Isobutene recovery % |
| 1 | 2 | 6 | 210 | 49.4 | 99.8 | 98.9 |
| 2 | 2 | 6 | 225 | 64.4 | 99.6 | 98.4 |
| 3 | 2 | 6 | 250 | 79.2 | 98.8 | 97.9 |
| 4 | 2 | 6 | 260 | 84.8 | 98.1 | 98.9 |

We claim:

1. A process for the preparation of tertiary olefins starting from the corresponding alkyl-tert.alkyl ethers, characterized in that the tert.alkyl ethers are reacted in the presence of a catalyst selected from the group consisting of a crystalline silica having a high specific surface area corresponding to the general formula 0–1M$_n$O$_m$. 1SiO$_2$, wherein M$_n$O$_m$ is the oxide of a metallic cation capable of entering into the silica lattice as a substituent for silicon or as a salt of polysilicic acids and/or an aluminum-modified silica corresponding to the general formula as follows:

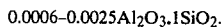

0.0006–0.0025Al$_2$O$_3$.1SiO$_2$.

2. Process according to claim 1, wherein the high-specific-surface-area crystalline silica has the general formula:

0.0001–1M$_n$O$_m$.1SiO$_2$.

3. Process according to claim 1 wherein the metallic cations which replace silicon are elements having an at least partially amphoteric nature, selected from the group consisting of chromium, beryllium, titanium, vanadium, manganese, iron, cobalt, zinc, zirconium, rhodium, silver, tin, antimony and boron.

4. Process according to claim 1 wherein the crystalline silica has a specific surface area of more than 150 m$^2$/g.

5. Process according to claim 1 characterized in that the tert.alkyl ethers are reacted under pressures of from 1 to 10 kg/cm$^2$ and at a temperature in the range of from 130° C. to 350° C.

6. Process according to claim 1 wherein the reaction is caused to take place at a space velocity (LHSV) of between 0.5 and 200.

7. Process according to claim 1 wherein the tertiary ether is methyl-tert.butyl ether.

8. Process according to claim 1 wherein the crystalline silica has a specific surface area of between 200 and 500 m$^2$/g.

9. Process according to claim 1 characterized in that the tert, alkyl ethers are reacted under pressure of from 1 to 10 kg/cm$^2$ and at a temperature of 500° C.

10. Process according to claim 1 wherein the reaction is caused to take place at a space velocity (LHSV) of between 1 and 50.

* * * * *